United States Patent [19]

Simon et al.

[11] Patent Number: 5,037,849

[45] Date of Patent: Aug. 6, 1991

[54] PHARMACEUTICAL COMPOSITIONS CONTAINING NITROXYALKYLAMINES, NOVEL NITROXYALKYLAMINES AND PROCESSES FOR THE PREPARATION THEREOF

[75] Inventors: Herbert Simon, Lampertheim; Helmut Michel; Michael Schultz, both of Mannheim; Wolfgang Bartsch, Viernheim, all of Fed. Rep. of Germany

[73] Assignee: Boehringer Mannheim GmBH, Mannheim, Fed. Rep. of Germany

[21] Appl. No.: 424,452

[22] Filed: Oct. 20, 1989

[30] Foreign Application Priority Data

Oct. 22, 1988 [DE] Fed. Rep. of Germany ....... 3836021

[51] Int. Cl.$^5$ ..................... A61K 31/21; C07C 205/10
[52] U.S. Cl. ...................................... 514/509; 558/483
[58] Field of Search .......................... 558/483; 514/509

[56] References Cited

U.S. PATENT DOCUMENTS

| | | | |
|---|---|---|---|
| 2,991,290 | 7/1961 | Shapiro et al. | 260/319 |
| 3,189,646 | 6/1965 | Rainer | 269/561 |
| 4,306,080 | 12/1981 | Haase et al. | 564/197 |
| 4,801,596 | 1/1989 | Simon et al. | 514/509 X |
| 4,863,949 | 9/1989 | Simon et al. | 558/483 X |

FOREIGN PATENT DOCUMENTS

| | | |
|---|---|---|
| 0090063 | 10/1983 | European Pat. Off. . |
| 0200915 | 12/1986 | European Pat. Off. . |
| 0280951 | 9/1988 | European Pat. Off. . |
| 3705622 | 9/1988 | Fed. Rep. of Germany . |
| 961317 | 6/1964 | United Kingdom . |
| 1602412 | 11/1981 | United Kingdom . |

OTHER PUBLICATIONS

Campbell and Behr, *J. Org. Chem.*, vol. 38, No. 6, pp. 1183–1186, 1973.

*Primary Examiner*—John S. Maples
*Assistant Examiner*—Chhaya Sayala
*Attorney, Agent, or Firm*—Armstrong, Nikaido, Marmelstein, Kubovcik & Murray

[57] ABSTRACT

The present invention provides pharmaceutical compositions effective against angina-like heart and circulatory diseases containing at least one nitroxyalkylamine derivative of the general formula:

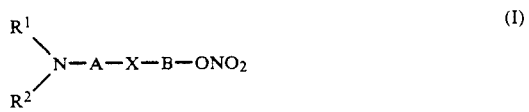

wherein $R_1$ is a hydrogen atom, a lower-alkyl radical, a $C_3$-$C_8$-cycloalkyl or $C_3$-$C_8$-cycloalkenyl radical, an aminocarbonyl, $C_1$-$C_6$-mono- or di-alkylaminocarbonyl radical, $R^2$ is a hydrogen atom, a lower-alkyl radical or a $C_3$-$C_8$-cycloalkyl or cycloalkenyl radical or $R^2$, together with $R^1$ and the nitrogen atom to which they are attached, form a heteroaliphatic ring containing up to 6 carbon atoms, A is a valency bond or a straight-chained or branched lower-alkylene radical, in which a —$CH_2$— group can be replaced by a cycloalkylene radical, B is a lower-alkylene radical, in which a —$CH_2$— group can be replaced by a cycloalkylene radical and X is an —$NR^3$—CO— or —CO—$NR^3$— radical, in which $R^3$ is a hydrogen atom or a lower-alkyl radical, when X is an —$NR^3$—CO— radical, $R^3$, together with the nitrogen atom and a carbon atom of the group A, bridge a heterocyclic ring containing 4 to 6 carbon atoms or $R^3$, together with $R^2$, A and the two nitrogen atoms, bridge a heterocyclic ring containing 3 to 5 carbon atoms; and the optically-active forms and physiologically acceptable salts thereof.

13 Claims, No Drawings

PHARMACEUTICAL COMPOSITIONS CONTAINING NITROXYALKYLAMINES, NOVEL NITROXYALKYLAMINES AND PROCESSES FOR THE PREPARATION THEREOF

The present invention is concerned with pharmaceutical compositions containing nitroxyalkylamines, as well as with new nitroxyalkylamines and processes for the preparation thereof.

The new pharmaceutical compositions according to the present invention contain, as active materials, at least one nitroxyalkylamine derivative of the general formula:

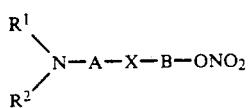

wherein $R^1$ is a hydrogen atom, a straight-chained or branched, saturated or unsaturated $C_1$-$C_8$-alkyl radical, a $C_3$-$C_8$-cycloalkyl or $C_3$-$C_8$-cycloalkenyl radical, an aminocarbonyl, $C_1$-$C_6$-alkylaminocarbonyl or di-$C_1$-$C_6$-alkylaminocarbonyl radical, $R^2$ is a hydrogen atom, a straight-chained or branched, saturated or unsaturated $C_1$-$C_6$-alkyl radical or a $C_3$-$C_8$-cycloalkyl or cycloalkenyl radical or $R^2$, together with $R^1$ and the nitrogen atom to which they are attached, form a heteroaliphatic ring containing up to 6 carbon atoms, wherein one or two carbon atoms can also be replaced by nitrogen or oxygen atoms, A is a valency bond or a straight-chained or branched alkylene chain containing up to 8 carbon atoms, in which a —$CH_2$— group can be replaced by a cycloalkylene radical containing 3 to 7 carbon atoms, B is a straight-chained or branched alkylene chain containing up to 8 carbon atoms, in which a —$CH_2$— group can be replaced by a cycloalkylene radical containing 3 to 7 carbon atoms and X is a —$NR^3$—CO— or —CO—$NR^3$— radical, in which $R^3$ is a hydrogen atom or a saturated or unsaturated alkyl radical containing up to 6 carbon atoms or, when X is a —$NR^3$—CO— radical, $R^3$, together with the nitrogen atom and a carbon atom of the group A, bridges a heterocyclic ring with 4 to 6 carbon atoms or $R^3$, together with $R^2$, A and the two nitrogen atoms, bridges a heterocyclic ring with 3 to 5 carbon atoms; and/or the optically-active forms, as well as physiologically acceptable salts thereof.

Compounds in which X is an —NH—CO— group and $R^1$ and $R^2$ are hydrogen atoms have already been described as intermediates in European Patent Specification No. 0,200,915 (cf. there compounds of general formula IV). For the case in which X is a —CO—$NR^3$— group and $R^1$ and $R^2$ are hydrogen atoms, then such compounds are known as intermediate products from European Patent Specification No. 0,280,951 (cf. there compounds of general formula IV). However, a pharmacological action is there not described. All the other compounds are new.

Consequently, the present invention also provides new compounds of the general formula:

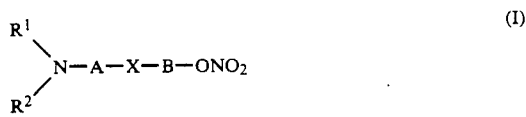

wherein $R^1$ is a hydrogen atom, a straight-chained or branched, saturated or unsaturated $C_1$-$C_8$-alkyl radical, a $C_3$-$C_8$-cycloalkyl or $C_3$-$C_8$-cycloalkenyl radical, an aminocarbonyl, $C_1$-$C_6$-alkylaminocarbonyl or di-$C_1$-$C_6$-alkylaminocarbonyl radical, $R^2$ is a hydrogen atom, a straight-chained or branched, saturated or unsaturated $C_1$-$C_6$-alkyl radical or a $C_3$-$C_8$-cycloalkyl or cycloalkenyl radical or $R^2$, together with $R^1$ and the nitrogen to which they are attached, form a heteroaliphatic ring containing up to 6 carbon atoms, wherein one or two carbon atoms can be replaced by nitrogen or oxygen atoms, A is a valency bond or a straight-chained or branched alkylene chain containing up to 8 carbon atoms, in which a —$CH_2$— group can be replaced by a cycloalkylene radical containing 3 to 7 carbon atoms, B is a straight-chained or branched alkylene chain containing up to 8 carbon atoms, in which a —$CH_2$— group can be replaced by a cycloalkylene radical containing 3 to 7 carbon atoms and X is a —$NR^3$—CO— or —CO—$NR^3$— radical, in which $R^3$ is a hydrogen atom or a saturated or unsaturated alkyl radical containing up to 6 carbon atoms or, when X is a —$NR^3$—CO— group, $R^3$, together with the nitrogen atom and a carbon atom of the group A, bridges a heterocyclic ring containing 4 to 6 carbon atoms or $R^3$, together with $R^2$, A and the two nitrogen atoms, bridge a heterocyclic ring containing 3 to 5 carbon atoms, with the proviso that $R^1$ and $R^2$ do not simultaneously signify hydrogen atoms when X is a —NH—CO— or —CO—$NR_3$— radical, as well as the optically-active forms and physiologically acceptable salts thereof.

The pharmaceutical compositions according to the present invention containing compounds of the general formula I possess valuable pharmacological properties. They bring about a reduction of the oxygen requirement of the heart, an increase of the blood flow and a lowering of the blood pressure. Surprisingly, we have now found that the compounds according to the present invention have a nitrate-like action with an especially long duration of action. Therefore, they can be used for the prophylaxis or treatment of heart and circulatory diseases, for example angina pectoris.

$R^1$ can be a hydrogen atom or a straight-chained, branched or cyclic alkyl chain containing up to 8 carbon atoms and preferably methyl, ethyl, n-propyl, isopropyl, n-butyl, n-pentyl, cyclopropyl, cyclopentyl, cyclohexyl and cycloheptyl, as well as, for example, isobutyl, 2-pentyl, 2-hexyl, n-heptyl, n-octyl, cyclobutyl and cyclooctyl. $R^1$ can also be an alkylaminocarbonyl radical, the methylaminocarbonyl, ethylaminocarbonyl, isopropylaminocarbonyl and tert.-butylaminocarbonyl radicals being preferred.

$R^2$ can be a hydrogen atom or a straight-chained, branched or cyclic alkyl chain containing up to 6 carbon atoms and preferably a methyl, ethyl, n-propyl, n-hexyl, cyclopentyl or cyclohexyl radical, as well as, for example, 2-butyl, isobutyl, 2-pentyl, 2-hexyl or cyclopropyl. Furthermore, $R^2$, together with $R^1$ and the neighbouring nitrogen atom, can form a heteroaliphatic ring containing 2 to 6 carbon atoms, in which 1 or 2 carbon atoms can also be replaced by nitrogen or oxygen atoms. As examples, there are to be mentioned the aziridine ring, the azetidine ring, the pyrrolidine ring, the piperidine ring, the perhydroazepine ring, the piperazine ring and the morpholine ring, the pyrrolidine, piperidine and morpholine rings thereby being especially preferred.

A can be a straight-chained alkylene chain containing up to 8 and preferably up to 5 carbon atoms, preferably methylene, ethylene, trimethylene, tetramethylene, pentamethylene, as well as hexamethylene, heptamethylene and octamethylene. The alkylene chain A can also be branched and contain 2 to 8 and preferably 2 to 5 carbon atoms. There are preferred, for example, methylmethylene, 1-methylethylene, dimethylmethylene, 1,1-dimethylethylene, 1,1-dimethyltrimethylene, 1-methyltrimethylene, as well as, for example, 1,1-dimethylmethylene, 1-ethylmethylene, 1,1-dimethyltetramethylene, 1,2-dimethyltrimethylene, 2,2-dimethyltrimethylene, 3,3-dimethyltrimethylene, 1,1-dimethylpentamethylene, 1,1-dimethylhexamethylene, 1-methyltetramethylene. A —$CH_2$— group or an alkylene group can be replaced by a cycloalkylene radical containing 3 to 7 and preferably 6 carbon atoms. In this case, there are preferred the 1,2-, 1,3- and 1,4-cyclohexylene radicals in which the position of the substituents can be cis or trans. Furthermore, there can be used, for example, the methylene-1,2-, -1,3- or -1,4-cyclohexylene radical, the methylene-1,2-, -1,3- or -1,4-cyclohexylenemethylene radical, the ethylene-1,2-, -1,3- or -1,4-cyclohexylene radical, the trimethylene-1,2-, -1,3- or -1,4-cyclohexylene radical, the tetramethylene-1,2-, -1,3- or -1,4-cyclohexylene radical or also the methylene-1,2-, -1,3- or -1,4-cyclohexyleneethylene radical or the ethylene-1,2-, -1,3- or -1,4-cyclohexylenetetramethylene radical in which the configuration of the cycloalkylene radical can be cis or trans. Further alkylene chains A are, for example, the 1,2-cyclopropylene radical, the methylene-1,2-cyclopropylene radical, the tetramethylene-1,2-cyclopropylene radical, the methylene-1,2-cyclopropylenemethylene radical, the methylene-1,2-cyclopropyleneethylene radical, the 1,2- or 1,3-cyclobutylene radical, the methylene-1,2- or -1,3-cyclobutylene radical, the tetramethylene-1,2- or -1,3-cyclobutylene radical, the methylene-1,2- or -1,3-cyclobutylenemethylene radical, the methylene-1,2- or -1,3-cyclobutyleneethylene radical, the 1,2- or 1,3-cyclopentylene radical, the methylene-1,2- or 1,3-cyclopentylene radical, the tetramethylene-1,2- or -1,3-cyclopentylene radical, the methylene-1,2- or -1,3-cyclopentylenemethylene radical, the methylene-1,2- or -1,3-cyclopentyleneethylene radical, the 1,2-, 1,3- or 1,4-cycloheptylene radical, the methylene-1,2-, -1,3- or -1,4-cycloheptylene radical, the tetramethylene-1,2-, -1,3- or -1,4-cycloheptylene radical, the methylene-1,2-, 1,3- or -1,4-cycloheptylene radical, the methylene-1,2-, -1,3- or -1,4-cycloheptyleneethylene radical, the configuration of the cycloalkylene radicals being cis or trans.

The group B can be a straight-chained or branched alkylene chain containing up to 8 and preferably 2 to 6 carbon atoms, preferably ethylene, 1-methylethylene, 2-methylethylene, trimethylene, 1-methyltrimethylene, 3-methyltrimethylene, tetramethylene, pentamethylene, 1-methyltetramethylene, 1-ethyltrimethylene, hexamethylene, 1-methylpentamethylene, 1-ethyltetramethylene, 1-n-propyl-trimethylene, 1,1-dimethylethylene, as well as, for example, dimethylmethylene, 1,1-dimethyltrimethylene, 2,2-dimethyltrimethylene, 2,2-dimethyltetramethylene or 1,1-dimethylhexamethylene. For the case in which a —$CH_2$— group of the chain B is replaced by a cycloalkylene radical containing 3 to 7 carbon atoms, there can be used, for example, the cyclopentylene radical, the 1,2-, 1,3- or 1,4-cyclohexylene radical, the methylene-1,2-cyclohexylene radical, the methylene-1,3-cyclohexylene radical or the methylene-1,4-cyclohexylene radical, in which the configuration of the cycloalkylene radical can be cis or trans.

$R^3$ can be a hydrogen atom or a straight-chained or branched, saturated or unsaturated alkyl radical containing up to 6 and especially up to 3 carbon atoms, preferably a methyl radical, an ethyl radical, an n-propyl radical, an isopropyl radical or an allyl radical, as well as, for example, an n-butyl radical or an isobutyl radical.

For the case in which X is an —$NR^3$—CO— radical and $R^3$, together with the nitrogen atom and a carbon atom of the group A, forms a heterocyclic ring, then this is preferably a pyrrolidine or piperidine ring. When $R^3$, together with $R^2$, A and the two nitrogen atoms, forms a heterocyclic ring, then the piperazine ring is especially preferred.

Preferred compounds of general formula I are those in which $R^1$ is a hydrogen atom, a straight-chained or branched $C_1$-$C_3$-alkyl radical, for example a methyl, ethyl or isopropyl radical, an aminocarbonyl group or a $C_1$-$C_3$-alkylaminocarbonyl radical, for example an isopropylaminocarbonyl radical, $R^2$ is a hydrogen atom or a straight-chained $C_1$-$C_3$-alkyl radical, for example a methyl or ethyl radical, or $R^2$, together with $R^1$ and the nitrogen atom, form a pyrrolidine, piperidine or morpholine ring, A is a straight-chained or branched alkylene chain containing up to 5 carbon atoms, for example methylene, ethylene, trimethylene, methylmethylene, dimethylmethylene, 1,1-dimethylethylene, 1,1-dimethyltrimethylene or 2,2-dimethyltrimethylene, B is a straight-chained or branched alkylene chain containing up to 6 carbon atoms, in which a —$CH_2$— group can be replaced by cyclohexylene, for example, methylene, ethylene, trimethylene, tetramethylene, pentamethylene, dimethylmethylene, 1,1-dimethylethylene, 2-methylethylene, 2,2-dimethyltrimethylene, 1-methyltrimethylene, 4-methyltetramethylene, cyclohexylene, methylcyclohexylene, ethylcyclohexylene or cyclohexylmethylene, and X is an —$NR^3$—CO— or —CO—$NR^3$— radical, in which $R^3$ is a hydrogen atom or, when X is an —$NR^3$—CO— radical, $R_3$, together with the two nitrogen atoms of the chain A and $R_2$, represents a piperazine ring.

The pharmaceutical compositions according to the present invention are usually administered in amounts of 20 to 500 mg. of active material per day, referred to a body weight of 75 kg. It is preferred to administer once or twice a day 1 or 2 tablets with a content of active material of 10 to 300 mg. The tablets can also be retarded whereby, per day, only 1 or 2 tablets have to be administered with 20 to 600 mg. of active material once per day. The active material can also be administered by injection 1 to 8 times a day or by continuous infusion, in which case amounts of from 5 to 200 mg./day normally suffice.

The compounds of general formula I can be prepared in known manner in that 1) a compound of the general formula:

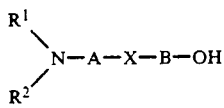  (II)

in which $R^1$, $R^2$, A, X and B have the above-given meanings, is subjected to a nitrate ester formation reaction; or 2.1) when X is an —$NR^3$—CO— radical, a compound of the general formula:

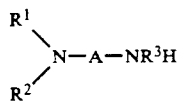  (III)

in which $R^1$, $R^2$, $R^3$ and A have the above-given meanings, is reacted with a compound of the general formula:

$$Z-CO-B-ONO_2 \quad (IV)$$

in which B has the above-given meaning and Z is a nucleofuge group, or 2.2) when X is a —CO—$NR^3$— radical, a compound of the general formula:

$$HNR^3-B-ONO_2 \quad (V)$$

in which B and $R^3$ have the above-given meanings, is reacted with a compound of the general formula:

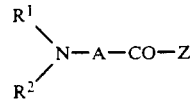  (IV)

in which A, $R^1$, $R^2$ and Z have the above-given meanings, or 2.3) a compound of the general formula:

$$R^2-NH-A-X-B-ONO_2 \quad (VII)$$

in which A, B, $R^2$ and X have the above-given meanings, is reacted with an isocyanate of the general formula $R^1$—NCO or a haloformic acid derivative of the general formula $R^1$—NH—CO—Hal, in which $R^1$ has the same meaning as above and Hal is a chlorine or bromine atom.

Compounds of general formula II, in which X is an —NH—CO— radical and $R^1$ and $R^2$ are hydrogen atoms are already known from European Patent Specification No. A-0,200,915 (cf. there compounds of general formula XIV). When X is a —CO—$NR^3$— radical and $R^1$ and $R^2$ are hydrogen atoms, then such compounds are described in European Patent Specification No. A-0,280,951 (cf. there compounds of the general formula XIII).

Some compounds of general formula II, in which $R^1$ and $R^2$ are not hydrogen atoms, are known from the literature and can be prepared by the processes described therein (cf. in this regard British Patent Specification No. 961,317; U.S. Pat. Nos. 4,308,080, 3,189,646 and 2,991,290, British Patent Specification No. 1,602,412 and European Patent Specification No. A-0,090,063).

However, compounds of general formula II in which B is a cycloalkylene radical are new and also the subject of the present invention.

Furthermore, compounds of general formula II, in which $R^1$ and $R^2$ are hydrogen atoms are known as intermediates from European Patent Specifications Nos. A-0,200,915 and A-0,280,951. Furthermore, some of these compounds are already known from the literature: 2-amino-N-(2-hydroxyethyl)-acetic acid amide oxalate from Helv. Chim. Acta, 38, 1342/1955 and 3-amino-N-(2-hydroxyethyl)-propionic acid amide from J. Chem. Soc., 1954, 2803.

The compounds of general formula II can be prepared in known manner in that 1) for the case in which X is an —$NR^3$—CO— radical
1.1) a compound of the general formula III is reacted with a compound of the general formula:

$$Z-CO-B-OH \quad (VIII)$$

wherein $R^1$, $R^2$, A, $R^3$, B and Z have the above-given meanings; or 1.2) a compound of the general formula III is reacted with a compound of the general formula:

$$Z-CO-B-O-W \quad (IX)$$

wherein $R^1$, $R^2$, A, $R^3$, B and Z have the above-given meanings and W is a protective group, whereafter the protective group is split off; or 1.3) a compound of the general formula III is reacted with a lactone of the general formula:

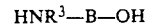  (X)

wherein $R^1$, $R^2$, A, $R^3$ and B have the above-given meanings;

2) for the case in which X is a —CO—$NR^3$ radical
2.1) a compound of the general formula VI is reacted with a compound of the general formula:

$$HNR^3-B-OH \quad (XI)$$

wherein $R^1$, $R^2$, A, Z, $R^3$ and B have the above-given meanings; or 2.2) a compound of the general formula VI is reacted with a compound of the general formula:

$$HNR^3-B-O-W \quad (XII)$$

wherein $R^1$, $R^2$, A, Z, $R^3$, B and W have the above-given meanings, and the protective group W is subsequently split off; or 2.3) a compound of the general formula:

$$V-A-CO-Z \quad (XIII)$$

in reacted with a compound of general formula XI, wherein A, Z, $R^3$ and B have the above-given meanings and V is a group which can be converted into an $R^1R^2N$— radical, and subsequently the group V is converted into an $R^1R^2N$— radical; or 2.4) a compound of the general formula XIII is reacted with a compound of general formula XII, wherein V, A, Z, $R^3$, B and W have the above-given meanings, whereafter the group V is converted into an $R^1R^2N-$ radical and the protective group W is split off.

The nitrate ester formation reaction of the compounds of general formulae II, VIII or XI can be carried out by reacting the compounds of general formulae II, VIII and XI with a nitrate ester-forming reagent, for example fuming nitric acid, a mixture of fuming nitric acid and acetic anhydride or a mixture of fuming nitric acid and concentrated sulphuric acid or nitrogen pentoxide at a low temperature in the presence of absence of an inert solvent. The reaction temperature is from ambient temperature to $-60°$ C. and preferably of from $-10°$ to $-30°$ C. The mole ratio of the reaction components is from 1 to 10.

Alternatively, the nitrate ester formation reaction can be carried out by selectively replacing in a compound of general formulae II, VIII or XI the aliphatic hydroxyl group by a halogen atom or by an alkyl- or arylsulphonic acid ester group and subsequently reacting the reaction product with, for example, silver nitrate or tetrabutylammonium nitrate in the presence or absence of a solvent at a temperature of from ambient temperature to 100° C. The mole ratio in the reaction between the halogen compound and silver nitrate can be from 1 to 10.

As nucleofugic group Z, there can be used alcoholates, halides or alkyl carboxylates. Therefore, the correspondingly activated carboxylic acids IV, VI, VIII, IX or XIII are present in the form of esters, carboxylic acid halides or anhydrides. However, the activation of the carboxylic acids can also be achieved by means of activating reagents, for example N,N'-carbonyldiimidazole, N,N'-dicyclohexylcarbodiimide, 1-ethyl-3-(3-dimethylaminopropyl)-carbodiimide, 1-alkyl-2-halopyridinium salts and the like. The molar ratio between the reaction components can be from 1 to 100.

As protective group W, there is preponderantly used the acetyl radical. However, in addition thereto, there can also be used, for example, the tetrahydropyranyl, benzyl or benzoyl radical. The splitting off of the protective group usually takes place in acidic or basic aqueous or alcoholic solution.

As protective group V, there can be used, for example, the $NO_2$ group, the azido group, the benzyl radical or the benzyloxycarbonyl radical or an amine group protected by 1 or 2 benzyl radicals. Furthermore, V can be a nucleofuge group, for example halide, mesylate or tosylate, which are reacted with benzyl group-protected primary and secondary amines or the amines $R^1R^2NH$. For the reduction of the $NO_2$ group, there can be used numerous processes, for example with zinc and hydrochloric acid, with iron in hydrochloric acid, with lithium aluminium hydride in ethers, with inorganic sulphides, such as sodium hydrogen sulphide, diammonium sulphide or sodium hydrosulphite in aqueous and/or alcoholic solution, or hydrogenolytically with catalysts, such as platinum dioxide, palladium or Raney nickel, preferably in an alcoholic solvent, such as methanol or ethanol, at a pressure of from 1 to 200 bar. The temperature used can be from $-20°$ C. to 200° C. and preferably from ambient temperature to 100° C. The reaction of amines with halides, mesylates or tosylates takes place in the presence or absence of a solvent at a temperature of from 0° C. to 150° C. and preferably of from 20° to 80° C. As solvents, there can be used, for example, methanol, ethanol, propanol, isopropanol, ethers, for example diethyl ether, diisopropyl ether, tert.-butyl methyl ether or tetrahydrofuran, or aromatic solvents, for example toluene or xylene. The molar ratio of the reaction components is not critical. There can be used ratios of from 1 to 100. The reactions can possibly be carried out under an elevated pressure. The splitting off of benzyl protective groups takes place hydrogenolytically in the presence of an organic solvent and/or of water, as well as of palladium on carbon as catalyst. The temperature used can be from ambient temperature to to 250° C. and preferably from ambient temperature to 60° C. and the hydrogen pressure used can be from 1 to 300 bar and preferably from 1 to 5 bar.

The compounds of general formula I can contain asymmetric carbon atoms. Therefore, the present invention also comprises all possible racemates and diastereomeric mixtures, as well as all optically-active forms of the compounds according to the present invention of general formulae I and II. Chiral compounds can be obtained either by direct synthesis or by conventional racemate separation.

For the conversion of compounds of general formula I into their pharmacologically acceptable salts, they are reacted, preferably in an organic solvent, with the equivalent amount of an inorganic or organic acids, for example hydrochloric acid, hydrobromic acid, nitric acid, phosphoric acid, sulphuric acid, formic acid, acetic acid, propionic acid, oxalic acid, fumaric acid, maleic acid, succinic acid, adipic acid, benzoic acid, salicylic acid, o-acetoxybenzoic acid, cinnamic acid, naphthoic acid, mandelic acid, citric acid, malic acid, tartaric acid, aspartic acid, glutamic acid, methanesulphonic acid, p-toluenesulphonic acid or N-cyclohexylaminesulphonic acid.

The compounds of general formula I can be administered as such or in the form of their salts enterally or parenterally in liquid or solid form. As injection medium, it is preferred to use water which contains the additives usual in the case of injection solutions, such as stabilising agents, solubilising agents or buffers. Additives of this type include, for example, tartrate and citrate buffers, ethanol, complex formers (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavouring and sweetening agents.

Besides the compounds described in the following Examples, the following compounds are, for example, also preferred according to the present invention:

2-amino-N-(2-methyl-5-nitroxypent-2-yl)-acetamide
2-dimethylamino-N-(2-methyl-4-nitroxybut-2-yl)-acetamide
L-2-amino-N-(2-nitroxyethyl)-propionic acid amide
L-2-amino-N-(2-methyl-1-nitroxyprop-2-yl)-propionic acid amide
L-2-amino-N-(3-nitroxypropyl)-propionic acid amide
2-amino-N-(2-methyl-1-nitroxyprop-2-yl)-propionic acid amide 2-amino-2-methyl-N-ethyl-N-(2-nitroxyethyl)-propionic acid amide
2-methylaminocarbonylamino-2-methyl-N-(2-nitroxyethyl)-propionic acid amide
2-aminocarbonylamino-2-methyl-N-(3-nitroxypropyl)-propionic acid amide
2-methylaminocarbonylamino-2-methyl-N-(3-nitroxypropyl)-propionic acid amide
2-[(2-methylethyl)-aminocarbonylamino]-2-methyl-N-(3-nitroxypropyl)-propionic acid amide
3-amino-N-(2-methyl-1-nitroxyprop-2-yl)-propionic acid amide
3-amino-N-(1-nitroxybut-3-yl)-propionic acid amide
3-amino-N-ethyl-N-(3-nitroxypropyl)-propionic acid amide
3-dimethylamino-N-(2-methyl-1-nitroxyprop-2-yl)-propionic acid amide
3-dimethylamino-N-(3-methyl-1-nitroxybut-3-yl)-propionic acid amide
3-amino-3-methyl-N-(3-nitroxypropyl)-butyric acid amide
4-amino-N-(2-methyl-1-nitroxyprop-2-yl)-butyric acid amide
4-amino-4-methyl-N-(2-methyl-1-nitroxyprop-2-yl)-valerianic acid amide
4-amino-4-methyl-N-(3-methyl-1-nitroxybut-3-yl)-valerianic acid amide
N-(2-aminoethyl)-2-nitroxypropionic acid amide
N-(2-aminoethyl)-3,3-dimethyl-5-nitroxyvalerianic acid amide
N-(2-aminocarbonylaminoethyl)-4-nitroxybutyric acid amide
N-(2-amino-2-methylpropyl)-2-nitroxypropionic acid amide
N-(2-dimethylaminoethyl)-2-nitroxypropionic acid amide
N-(2-dimethylaminoethyl)-2-methyl-2-nitroxypropionic acid amide
N-(2-dimethylaminoethyl)-2,2-dimethyl-3-nitroxypropionic acid amide
N-(2-dimethylaminoethyl)-3-nitroxybutyric acid amide
N-(2-diethylaminoethyl)-2-nitroxypropionic acid amide
N-(2-diethylaminoethyl)-2-methyl-2-nitroxypropionic acid amide
N-(2-diethylaminoethyl)-2,2-dimethyl-3-nitroxypropionic acid amide
N-(2-diethylaminoethyl)-3,3-dimethyl-5-nitroxyvalerianic acid amide
2-methyl-2-nitroxy-N-[2-(1-pyrrolidino)-ethyl]-propionic acid amide
2,2-dimethyl-3-nitroxy-N-[2-(1-pyrrolidino)-ethyl]-propionic acid amide
3-nitroxy-N-[2-(1-pyrrolidino)-ethyl]-butyric acid amide
4-nitroxy-N-[2-(1-pyrrolidino)-ethyl]-butyric acid amide
5-nitroxy-N-[2-(1-pyrrolidino)-ethyl]-valerianic acid amide
2-nitroxy-N-[2-(1-piperidino)-ethyl]-propionic acid amide
2,2-dimethyl-3-nitroxy-N-[2-(1-piperidino)-ethyl]-propionic acid amide
4-nitroxy-N-[2-(1-piperidino)-ethyl]-butyric acid amide
5-nitroxy-N-[2-(1-piperidino)-ethyl]-valerianic acid amide
3,3-dimethyl-5-nitroxy-N-[2-(1-piperidino)-ethyl]-valerianic acid amide
N-[2-(4-morpholino)-ethyl]-2-nitroxypropionic acid amide
2-methyl-N-[2-(4-morpholino)-ethyl]-2-nitroxypropionic acid amide
2,2-dimethyl-N-[2-(4-morpholino)-ethyl]-3-nitroxypropionic acid amide
N-(3-aminopropyl)-2,2-dimethyl-3-nitroxypropionic acid amide
4-nitroxybutyric acid piperazide
4-nitroxyvalerianic acid piperazide
2-nitroxypropionic acid 4-methyl piperazide
2-methyl-2-nitroxypropionic acid 4-methylpiperazide
2,2-dimethyl-3-nitroxypropionic acid 4-methylpiperazide
4-nitroxybutyric acid 4-methylpiperazide
5-nitroxyvalerianic acid 4-methylpiperazide
cis-2-amino-N-(4-nitroxycyclohexyl)-acetamide
cis-2-amino-N-(4-nitroxycyclohexylmethyl)-acetamide
trans-2-amino-N-(4-nitroxymethylcyclohexyl)-acetamide
cis-2-amino-N-(4-nitroxymethylcyclohexyl)-acetamide
trans-2-dimethylamino-N-(2-nitroxycyclohexyl)-acetamide
cis-2-dimethylamino-N-(4-nitroxycyclohexyl)-acetamide
trans-2-dimethylamino-N-(4-nitroxycyclohexylmethyl)-acetamide
trans-2-dimethylamino-N-(4-nitroxymethylcyclohexyl)-acetamide
cis-2-dimethylamino-N-(4-nitroxymethylcyclohexyl)-acetamide
L-trans-2-amino-N-(4-nitroxycyclohexyl)-propionic acid amide
L-cis-2-amino-N-(4-nitroxycyclohexyl)-propionic acid amide
L-trans-2-amino-N-(4-nitroxycyclohexylmethyl)-propionic acid amide
L-cis-2-amino-N-(4-nitroxycyclohexylmethyl)-propionic acid amide
L-trans-2-amino-N-(4-nitroxymethylcyclohexyl)-propionic acid amide
L-cis-2-amino-N-(4-nitroxymethylcyclohexyl)-propionic acid amide
trans-3-amino-N-(2-nitroxycyclohexyl)-propionic acid amide
cis-3-amino-N-(4-nitroxycyclohexyl)-propionic acid amide
trans-3-amino-N-(4-nitroxycyclohexylmethyl)-propionic acid amide
cis-3-amino-N-(4-nitroxycyclohexylmethyl)-propionic acid amide
trans-3-amino-N-(4-nitroxymethylcyclohexyl)-propionic acid amide
cis-3-amino-N-(4-nitroxymethylcyclohexyl)-propionic acid amide
trans-3-dimethylamino-N-(2-nitroxycyclohexyl)-propionic acid amide
cis-3-dimethylamino-N-(4-nitroxycyclohexyl)-propionic acid amide
trans-3-dimethylamino-N-(4-nitroxycyclohexylmethyl)-propionic acid amide
cis-3-dimethylamino-N-(4-nitroxycyclohexylmethyl)-propionic acid amide
trans-3-dimethylamino-N-(4-nitroxymethylcyclohexyl)-propionic acid amide
cis-3-dimethylamino-N-(4-nitroxymethylcyclohexyl)-propionic acid amide trans-3-amino-3-methyl-N-(2-nitroxycyclohexyl)-butyric acid amide
trans-3-amino-3-methyl-N-(4-nitroxycyclohexyl)-butyric acid amide
cis-3-amino-3-methyl-N-(4-nitroxycyclohexyl)-butyric acid amide
trans-3-amino-3-methyl-N-(4-nitroxycyclohexylmethyl)-butyric acid amide
trans-3-amino-3-methyl-N-(4-nitroxymethylcyclohexyl)-butyric acid amide
cis-3-amino-3-methyl-N-(4-nitroxymethylcyclohexyl)-butyric acid amide
trans-N-(2-aminoethyl)-2-(4-nitroxycyclohexyl)-acetamide
cis-N-(2-aminoethyl)-2-(4-nitroxycyclohexyl)-acetamide
trans-N-(2-amino-2-methylpropyl)-2-(4-nitroxycyclohexyl)-acetamide
cis-N-(2-amino-2-methylpropyl)-2-(4-nitroxycyclohexyl)-acetamide
trans-N-(2-dimethylaminoethyl)-4-nitroxycyclohexanecarboxylic acid amide
trans-N-(2-dimethylaminoethyl)-2-(4-nitroxycyclohexyl)-acetamide
cis-N-(2-dimethylaminoethyl)-2-(4-nitroxycyclohexyl)-acetamide
trans-N-(2-diethylaminoethyl)-2-(2-nitroxycyclohexyl)-acetamide
trans-N-(2-diethylaminoethyl)-2-(4-nitroxycyclohexyl)-acetamide
cis-N-(2-diethylaminoethyl)-2-(4-nitroxycyclohexyl)-acetamide
trans-2-(4-nitroxycyclohexyl)-N-[2-(1-pyrrolidino)-ethyl]-acetamide
cis-2-(4-nitroxycyclohexyl)-N-[2-(1-pyrrolidino)-ethyl]-acetamide
trans-2-(4-nitroxycyclohexyl)-N-[2-(1-piperidino)-ethyl]-acetamide
cis-2-(4-nitroxycyclohexyl)-N-[2-(1-piperidino)-ethyl]-acetamide
cis-N-[2-(4-morpholino)-ethyl]-2-(4-nitroxycyclohexyl)-acetamide
trans-N-(3-aminopropyl)-2-(4-nitroxycyclohexyl)-acetamide
cis-N-(3-aminopropyl)-2-(4-nitroxycyclohexyl)-acetamide
trans-N-(3-amino-2,2-dimethylpropyl)-2-(4-nitroxycyclohexyl)-acetamide
cis-N-(3-amino-2,2-dimethylpropyl)-2-(4-nitroxycyclohexyl)-acetamide
cis-4-nitroxycyclohexanecarboxylic acid piperazide
cis-2-(4-nitroxycyclohexyl)-acetic acid piperazide
cis-4-nitroxycyclohexanecarboxylic acid 4-methylpiperazide
cis-2-(4-nitroxycyclohexyl)acetic acid 4-methylpiperazide
4-nitroxybutyric acid 4-aminocarbonylaminopiperidide
2,2-dimethyl-3-nitroxypropionic acid 4-aminocarbonylaminopiperidide
5-nitroxyvalerianic acid 4-aminocarbonylaminopiperidide
4-nitroxybutyric acid 4-aminocarbonylpiperazide
trans-N-(2-nitroxycyclohexylmethyl)-urea.

The following Examples are given for the purpose of illustrating the present invention:

EXAMPLE 1

3-Amino-N-(3-nitroxypropyl)-propionic acid amide fumarate 28.7 g. 3-Amino-N-(3-hydroxypropyl)-propionic acid amide hemioxalate are introduced, while stirring at 5° C., into 63 ml. 100% nitric acid. The reaction solution is further stirred for about 1 hour in an ice bath at +5° C., 1 liter of methylene chloride is then added thereto and neutralised, while further stirring, with 234 g. potassium carbonate sesquihydrate. After stirring for 1 hour in an ice bath, 100 ml. ethanol are added thereto and stirring continued for about 18 hours at ambient temperature. The suspension is filtered off with suction and the filtrate distilled in a vacuum at a maximum temperature of 20° C., about 32 g. of crude base remaining behind. By dissolving in ethanol and adding 17.4 g. fumaric acid, there are obtained 23 g. of the fumarate of the title compound, i.e. 50% of theory; m.p. 119°-120° C.

According to the process described in Example 1, the following compounds are obtained in an analogous way:

1) 2-amino-N-(2-nitroxyethyl)-acetamide fumarate from 2-amino-N-(2-hydroxyethyl)-acetamide oxalate; yield 20% of theory; solvent: ethanol/diethyl ether; m.p. 123°-125° C.

2) 2-amino-N-(1-nitroxy-2-methylprop-2-yl)-acetamide fumarate from 2-amino-N-(1-hydroxy-2-methylprop-2-yl)-acetamide oxalate; yield 70% of theory; solvent: ethanol; m.p. 142°-145° C.

3) 2-amino-N-(3-nitroxypropyl)-acetamide fumarate from 2-amino-N-(3-hydroxypropyl)-acetamide oxalate; yield 38% of theory; solvent: ethanol; m.p. 122°-124° C.

4) 2-amino-N-(2,2-dimethyl-3-nitroxypropyl)-acetamide fumarate from 2-amino-N-(2,2-dimethyl-3-hydroxypropyl)-acetamide oxalate; yield 30% of theory; solvent: ethanol; m.p. 146°-151° C.

5) 2-dimethylamino-N-(2-nitroxyethyl)-acetamide fumarate from 2-dimethylamino-N-(2-hydroxyethyl)-acetamide oxalate; yield 90% of theory; solvent: ethanol; m.p. 111°-113° C.

6) 2-amino-N-(2-nitroxyethyl)-propionic acid amide fumarate from 2-amino-N-(2-hydroxyethyl)-propionic acid amide oxalate; yield 15% of theory; solvent: ethanol; m.p. 114°-120° C.

7) 2-amino-2-methyl-N-(2-nitroxyethyl)-propionic acid amide fumarate from 2-amino-2-methyl-N-(2-hydroxyethyl)-propionic acid amide oxalate; yield 66% of theory; solvent: ethanol; m.p. 126° C.

8) 2-amino-2-methyl-N-(3-nitroxy-2-methylprop-2-yl)-propionic acid amide fumarate from 2-amino-2-methyl-N-(3-hydroxy-2-methylprop-2-yl)-propionic acid amide oxalate; yield 50% of theory; solvent: ethanol; m.p. 137°-138° C.

9) 2-amino-2-methyl-N-(3-nitroxypropyl)-propionic acid amide fumarate from 2-amino-2-methyl-N-(3-hydroxypropyl)-propionic acid amide; yield 22% of theory; solvent: ethanol; m.p. 133°-134° C.

10) 2-amino-2-methyl-N-(1-nitroxybut-3-yl)-propionic acid amide fumarate from 2-amino-2-methyl-N-(1-hydroxybut-3-yl)-propionic acid amide; yield 33% of theory; solvent: ethanol; m.p. 142°-146° C.

11) 3-amino-N-(2-nitroxyethyl)-propionic acid amide fumarate from 3-amino-N-(2-hydroxyethyl)-propionic acid amide oxalate; yield 22% of theory; solvent: ethanol; m.p. 117°-119° C.

12) 3-dimethylamino-N-(3-nitroxypropyl)-propionic acid amide from 3-dimethylamino-N-(3-hydroxypropyl)-propionic acid amide; yield 30% of theory; solvent: ethanol; m.p. 82°-85° C.
13) 3-amino-3-methyl-N-(2-nitroxyethyl)-butyric acid amide oxalate from 3-amino-3-methyl-N-(2-hydroxyethyl)-butyric acid amide oxalate; yield 30% of theory; solvent: acetone; m.p. 117°-123° C.
14) 4-amino-N-(2-nitroxyethyl)-butyric acid amide fumarate from 4-amino-N-(2-hydroxyethyl)-butyric acid amide oxalate; yield 25% of theory; solvent: ethanol; m.p. 99°-100° C.
15) 4-amino-N-(3-nitroxypropyl)-butyric acid amide fumarate from 4-amino-N-(3-hydroxypropyl)-butyric acid amide oxalate; yield 30% of theory; solvent: ethanol; m.p. 112°-113° C.
16) 4-amino-4-methyl-N-(2-nitroxyethyl)-valerianic acid amide hemifumarate from 4-amino-4-methyl-N-(2-hydroxyethyl)-valerianic acid amide oxalate; yield 29% of theory; solvent: acetone; m.p. 116°-119° C.
17) 4-amino-4-methyl-N-(3-nitroxypropyl)-valerianic acid amide fumarate from 4-amino-4-methyl-N-(3-hydroxypropyl)-valerianic acid amide hemioxalate; yield 68% of theory; solvent: ethyl acetate/acetone; m.p. 102° C. (decomp.).
18) N-(2-aminoethyl)-2-methyl-2-nitroxypropionic acid amide fumarate from N-(2-aminoethyl)-2-methyl-2-hydroxypropionic acid amide; yield 26% of theory; solvent: ethanol; m.p. 125°-127° C.
19) N-(2-aminoethyl)-2,2-dimethyl-3-nitroxypropionic acid amide fumarate from N-(2-aminoethyl)-2,2-dimethyl-3-hydroxypropionic acid amide oxalate; yield 80% of theory; solvent: ethanol; m.p. 158°-160° C.
20) N-(2-aminoethyl)-3-nitroxybutyric acid amide fumarate from N-(2-aminoethyl)-3-hydroxybutyric acid amide; yield 50% of theory; solvent: ethanol; m.p. 126°-128° C.
21) N-(2-aminoethyl)-4-nitroxybutyric acid amide from N-(2-aminoethyl)-4-hydroxybutyric acid amide; yield 63% of theory; solvent: ethanol; m.p. 105°-106° C.
22) N-(2-aminoethyl)-2-methyl-4-nitroxybutyric acid amide fumarate from N-(2-aminoethyl)-2-methyl-4-hydroxybutyric acid amide oxalate; yield 65% of theory; solvent: ethyl acetate; m.p. 64°-67° C.
23) N-(2-aminoethyl)-5-nitroxyvalerianic acid amide fumarate from N-(2-aminoethyl)-5-hydroxyvalerianic acid amide oxalate; yield 60% of theory; solvent: ethanol; m.p. 75° C.
24) N-(2-amino-2-methylpropyl)-2-methyl-2-nitroxypropionic acid amide fumarate from N-(2-amino-2-methylpropyl)-2-methyl-2-hydroxypropionic acid amide; yield 41% of theory; solvent: acetone; m.p. 150°-152° C.
25) N-(2-amino-2-methylpropyl)-2,2-dimethyl-3-nitroxypropionic acid amide fumarate from N-(2-amino-2-methylpropyl)-2,2-dimethyl-3-hydroxypropionic acid amide oxalate; yield 52% of theory; solvent: ethyl acetate; m.p. 150°-155° C.
26) N-(2-amino-2-methylpropyl)-3-nitroxybutyric acid amide fumarate from N-(2-amino-2-methylpropyl)-3-hydroxybutyric acid amide oxalate; yield 53% of theory; solvent: ethyl acetate; m.p. 128°-130° C.
27) N-(2-amino-2-methylpropyl)-4-nitroxybutyric acid amide fumarate from N-(2-amino-2-methylpropyl)-2-hydroxybutyric acid amide oxalate; yield 38% of theory; solvent: ethyl acetate; m.p. 175°-178° C.
28) N-(2-amino-2-methylpropyl)-5-nitroxycapronic acid amide fumarate from N-(2-amino-2-methylpropyl)-5-hydroxycapronic acid amide oxalate; yield 85% of theory; solvent: ethyl acetate; m.p. 60°-65° C.
29) N-(2-amino-2-methylpropyl)-5-nitroxyvalerianic acid amide hemifumarate from N-(2-amino-2-methylpropyl)-5-hydroxyvalerianic acid amide oxalate; yield 17% of theory; solvent: ethyl acetate/isopropanol; m.p. 128°-132° C.
30) N-(2-amino-2-methylpropyl)-3,3-dimethyl-5-nitroxyvalerianic acid amide fumarate from N-(2-amino-2-methylpropyl)-3,3-dimethyl-5-hydroxyvalerianic acid amide oxalate; yield 38% of theory; solvent: ethyl acetate; m.p. 104°-107° C.
31) N-(2-amino-2-methylpropyl)-6-nitroxycapronic acid amide fumarate from N-(2-amino-2-methylpropyl)-6-hydroxycapronic acid amide oxalate; yield 21% of theory; solvent: ethyl acetate/acetone; m.p. 95°-100° C.
32) N-(2-dimethylaminoethyl)-5-nitroxyvalerianic acid amide cyclamate from N-(2-dimethylaminoethyl)-5-hydroxyvalerianic acid amide oxalate; yield 18% of theory; solvent: ethyl acetate; m.p. 58°-60° C.
33) N-(2-diethylaminoethyl)-4-nitroxybutyric acid amide fumarate from N-(2-diethylaminoethyl)-4-hydroxybutyric acid amide oxalate; yield 24% of theory; solvent: ethyl acetate; m.p. 148°-150° C.
34) 2-nitroxy-N-[2-(1-pyrrolidino)-ethyl]-propionic acid amide fumarate from 2-hydroxy-N-[2-(1-pyrrolidino)-ethyl]-propionic acid amide oxalate; yield 60% of theory; solvent: ethanol; m.p. 98°-100° C.
35) N-(3-aminopropyl)-2-nitroxypropionic acid amide fumarate from N-(3-aminopropyl)-2-hydroxypropionic acid amide oxalate; yield 24% of theory; solvent: ethanol; m.p. 118°-121° C.
36) N-(3-aminopropyl)-2-methyl-2-nitroxypropionic acid amide fumarate from N-(3-aminopropyl)-2-methyl-2-hydroxypropionic acid amide oxalate; yield 15% of theory; solvent: ethanol; m.p. 147°-149° C.
37) N-(3-aminopropyl)-4-nitroxybutyric acid amide fumarate from N-(3-aminopropyl)-4-hydroxybutyric acid amide oxalate; yield 60% of theory; solvent: ethanol; m.p. 102°-105° C.
38) N-(3-amino-2,2-dimethylpropyl)-2-methyl-2-nitroxypropionic acid amide hemifumarate from N-(3-amino-2,2-dimethylpropyl)-2-methyl-2-hydroxypropionic acid amide oxalate; yield 57% of theory; solvent: ethanol/diethyl ether; m.p. 156°-158° C.
39) N-(3-amino-2,2-dimethylpropyl)-2,2-dimethyl-3-nitroxypropionic acid amide hemifumarate from N-(3-amino-2,2-dimethylpropyl)-2,2-dimethyl-3-hydroxypropionic acid amide oxalate; yield 30% of theory; solvent: ethanol/diethyl ether; m.p. 154°-157° C.
40) N-(3-amino-2,2-dimethylpropyl)-5-nitroxyvalerianic acid amide fumarate from N-(3-amino-2,2-dimethylpropyl)-5-hydroxyvalerianic acid oxalate; yield 70% of theory; solvent: ethyl acetate; m.p. 56°-60° C.
41) trans-2-amino-N-(2-nitroxycyclohexyl)-acetamide fumarate from trans-2-amino-N-(2-hydroxycyclohexyl)-acetamide; yield 16% of theory; solvent: acetone; m.p. 166°-168° C.
42) trans-2-amino-N-(4-nitroxycyclohexyl)-acetamide fumarate from trans-2-amino-N-(4-hydroxycyclohexyl)-acetamide; yield 20% of theory; solvent: ethanol; m.p. 160°-162° C.
43) trans-2-amino-N-(2-nitroxycyclohexylmethyl)-acetamide fumarate from trans-2-amino-N-(2-hydroxycyclohexylmethyl)-acetamide; yield 10% of theory; solvent: ethanol; m.p. 125°–127° C.

44) trans-2-amino-N-[2-(2-nitroxycyclohexyl)-ethyl]-acetamide fumarate from trans-2-amino-N-[2-(2-hydroxycyclohexyl)-ethyl]-acetamide; yield 19% of theory; solvent: ethanol; m.p. 86°–90° C.

45) trans-2-amino-2-methyl-N-(2-nitroxycyclohexylmethyl)-propionic acid amide fumarate from trans-2-amino-2-methyl-N-(2-hydroxycyclohexylmethyl)-propionic acid amide oxalate; yield 20% of theory; solvent: ethanol; m.p. 174°–177° C.

46) trans-2-amino-2-methyl-N-[2-(2-nitroxycyclohexyl)-ethyl]-propionic acid amide fumarate from trans-2-amino-2-methyl-N-[2-(2-hydroxycyclohexyl)-ethyl]-propionic acid-amide oxalate; yield 36% of theory; solvent: ethanol; m.p. 167°–170° C.

47) trans-3-amino-N-(4-nitroxycyclohexyl)-propionic acid amide fumarate from trans-3-amino-N-(4-hydroxycyclohexyl)-propionic acid amide; yield 27% of theory; solvent: ethyl acetate; m.p. 105°–110° C.

48) trans-N-(2-aminoethyl)-4-nitroxycyclohexanecarboxylic acid amide fumarate from trans-N-(2-aminoethyl)-4-hydroxycyclohexanecarboxylic acid amide; yield 21% of theory; solvent: ethanol; m.p. 84°–86° C.

49) trans-N-(2-aminoethyl)-2-(2-nitroxycyclohexyl)-acetamide fumarate from trans-N-(2-aminoethyl)-2-(2-hydroxycyclohexyl)-acetamide; yield 85% of theory; solvent: ethanol; m.p. 78°–80° C.

50) trans-N-(2-amino-2-methylpropyl)-4-nitroxycyclohexanecarboxylic acid amide fumarate from trans-N-(2-amino-2-methylpropyl)-2-hydroxycyclohexanecarboxylic acid amide; yield 61% of theory; solvent: ethyl acetate; m.p. 140°–143° C.

51) cis-N-(2-amino-2-methylpropyl)-4-nitroxycyclohexanecarboxylic acid amide hemifumarate from trans-N-(2-amino-2-methylpropyl)-2-hydroxycyclohexanecarboxylic acid amide; yield 45% of theory; solvent: ethanol; m.p. 182°–184° C.

52) trans-N-(2-amino-2-methylpropyl)-2-(2-nitroxycyclohexyl)-acetamide fumarate from trans-N-(2-amino-2-methylpropyl)-2-(2-hydroxycyclohexyl)-acetamide; yield 38% of theory; solvent: acetone; m.p. 150°–152° C.

53) trans-N-(2-dimethylaminoethyl)-2-(2-nitroxycyclohexyl)-acetamide cyclamate from trans-N-(2-dimethylaminoethyl)-2-(2-hydroxycyclohexyl)-acetamide oxalate; yield 54% of theory; solvent: ethyl acetate; m.p. 90°–93° C.

54) trans-N-(2-diethylaminoethyl)-4-nitroxycyclohexanecarboxylic acid amide fumarate from trans-N-(2-diethylaminoethyl)-4-hydroxycyclohexanecarboxylic acid amide oxalate; yield 20% of theory; solvent: acetone; m.p. 93°–96° C.

55) trans-N-[2-(1-pyrrolidinyl)-ethyl]-4-nitroxycyclohexanecarboxylic acid amide fumarate from trans-N-[2-(1-pyrrolidinyl)-ethyl]-4-hydroxycyclohexanecarboxylic acid amide; yield 17% of theory; solvent: ethanol; m.p. 126°–127° C.

56) cis-N-[2-(1-pyrrolidinyl)-ethyl]-4-nitroxycyclohexanecarboxylic acid amide maleate from cis-N-[2-(1-pyrrolidinyl)-ethyl]-4-hydroxycyclohexanecarboxylic acid amide; yield 33% of theory; solvent: acetone/diethyl ether; m.p. 91°–93° C.

57) trans-N-[2-(1-piperidinyl)-ethyl]-4-nitroxycyclohexanecarboxylic acid amide fumarate from trans-N-[2-(1-piperidinyl)-ethyl]-4-hydroxycyclohexanecarboxylic acid amide; yield 15% of theory; solvent: ethanol; m.p. 154°–155° C.

58) cis-N-[2-(1-piperidinyl)-ethyl]-4-nitroxycyclohexanecarboxylic acid amide maleate from cis-N-[2-(1-piperidinyl)-ethyl]-4-hydroxycyclohexanecarboxylic acid amide; yield 15% of theory; solvent: acetone/diethyl ether; m.p. 98°–100° C.

59) cis-N-(3-aminopropyl)-4-nitroxycyclohexanecarboxylic acid amide hemifumarate from cis-N-(3-aminopropyl)-4-hydroxycyclohexanecarboxylic acid amide; yield 10% of theory; solvent: ethanol; m.p. 148°–151° C.

60) trans-2-dimethylamino-N-(4-nitroxycyclohexyl)-acetamide fumarate from trans-2-dimethylamino-N-(4-hydroxycyclohexyl)-acetamide oxalate; yield 62% of theory; solvent: ethanol; m.p. 146°–147° C.

61) trans-N-[2-(4-morpholino)-ethyl]-4-nitroxycyclohexanecarboxylic acid amide hemifumarate from trans-N-[2-(4-morpholino)-ethyl]-4-hydroxycyclohexanecarboxylic acid amide oxalate; yield 35% of theory; solvent: ethanol; m.p. 146°–147° C.

62) trans-4-nitroxycyclohexanecarboxylic acid 4-methylpiperazide fumarate from trans-4-hydroxycyclohexanecarboxylic acid 4-methylpiperazide oxalate; yield 60% of theory; solvent: ethanol; m.p. 168°–170° C.

63) trans-N-(3-amino-2,2-dimethylpropyl)-4-nitroxycyclohexanecarboxylic acid amide fumarate from trans-N-(3-amino-2,2-dimethylpropyl)-4-hydroxycyclohexanecarboxylic acid amide oxalate; yield 25% of theory; solvent: ethanol; m.p. 126°–127° C.

64) 2-dimethylamino-N-(3-nitroxypropyl)-acetamide fumarate from 2-dimethylamino-N-(3-hydroxypropyl)-acetamide; yield 51% of theory; solvent: ethanol; m.p. 112°–115° C.

65) 3-dimethylamino-N-(2-nitroxyethyl)-propionic acid amide fumarate from 3-dimethylamino-N-(2-hydroxyethyl)-propionic acid amide; yield 30% of theory; solvent: ethanol; m.p. 105°–107° C.

66) trans-3-dimethylamino-N-(4-nitroxycyclohexyl)-propionic acid amide fumarate from trans-3-dimethylamino-N-(4-hydroxycyclohexyl)-propionic acid amide; yield 30% of theory; solvent: ethanol; m.p. 154°–156° C.

67) N-[2-(4-morpholino)-ethyl]-4-nitroxybutyric acid amide fumarate from N-[2-(4-morpholino)-ethyl]-4-hydroxybutyric acid amide; yield 50% of theory; solvent: ethanol; m.p. 96°–97° C.

68) cis-N-(2-dimethylaminoethyl)-4-nitroxycyclohexanecarboxylic acid amide fumarate from cis, N-(2-dimethylaminoethyl)-4-hydroxycyclohexanecarboxylic acid amide; yield 25% of theory; solvent: ethyl acetate; m.p. 78°–80° C.

69) cis-N-(2-diethylaminoethyl)-4-nitroxycyclohexanecarboxylic acid amide from cis-N-(2-diethylaminoethyl)-4-hydroxycyclohexanecarboxylic acid amide; yield 20% of theory; solvent: diethyl ether; m.p. 50°–51° C.

70) cis-N-[2-(4-morpholino)-ethyl]-4-nitroxycyclohexanecarboxylic acid amide fumarate from cis-N-(4-morpholino)-ethyl]-4-hydroxycyclohexanecarboxylic acid amide; yield 10% of theory; solvent: ethanol; m.p. 114°–116° C.

71) cis-N-(3-amino-2,2-dimethylpropyl)-4-nitroxycyclohexanecarboxylic acid amide fumarate from cis-N-(3-amino-2,2-dimethylpropyl)-4-hydroxycyclohexanecarboxylic acid amide; yield 50% of theory; solvent: ethanol/ethyl acetate; m.p. 130°–135° C.

72) trans-4-nitroxycyclohexanecarboxylic acid piperazide hemifumarate from trans-4-hydroxycyclohexanecarboxylic acid piperazide; yield 75% of theory; solvent: ethanol; m.p. 136°–138° C.

EXAMPLE 2

N-(2-Aminoethyl)-4-nitroxybutyric acid amide oxalate

In a 1 liter three-necked flask, 21.9 g. N-(2-aminoethyl)-4-hydroxybutyric acid amide are suspended in 300 ml acetonitrile and cooled in an ice-bath at +5° C. By the addition 9.5 ml. 100% nitric acid in 100 ml. acetonitrile (mixed in an ice-bath at 5°–10° C.), the base is converted into the nitric acid salt. To this suspension is now added dropwise a solution of acetyl nitrate in acetonitrile, mixed in an ice-bath, within the course of 30 minutes at 5° to 7° C., a clear solution thereby being formed. The reaction mixture is further stirred in an ice-bath for 1 hour.

1 liter tert.-butyl methyl ether in a 2 liter three-necked flask is cooled in an ice-bath to 5°–7° C. While stirring, the above-obtained reaction solution is run in in a thin stream. The product precipitates out as oily nitric acid salt and the supernatant solution is decanted off. To the oily residue is added a mixture of 675 ml. methylene chloride and 75 ml. ethanol and neutralised with 31.1 g. potassium carbonate to which 4.1 ml. of water had previously been added. The reaction mixture is left to stir overnight. The inorganic salts are filtered off with suction and washed three times with, in each case, 50 ml. methylene chloride. A solution of 13.5 g. oxalic acid in 40 ml. ethanol is added to the filtrate. The precipitate is filtered off with suction, washed with methylene chloride and diethyl ether and dried. There are obtained 25.8 g. of crystals of the desired product, i.e. 61% of theory; m.p. 102°–103° C.

The following compounds are obtained in an analogous manner:

1) 2-amino-2-methyl-N-(2-nitroxypropyl)-propionic acid amide hemifumarate from 2-amino-2-methyl-N-(2-hydroxypropyl)-propionic acid amide oxalate; yield 16% of theory; solvent: ethanol; m.p. 128°–131° C.

2) 2-amino-2-methyl-N-(2,2-dimethyl-3-nitroxypropyl)-propionic acid amide hemifumarate from 2-amino-2-methyl-N-(2,2-dimethyl-3-hydroxypropyl)-propionic acid amide oxalate; yield 27% of theory; solvent: ethanol; m.p. 157°–159° C.

3) N-(3-amino-2,2-dimethylpropyl)-4-nitroxybutyric acid amide fumarate from N-(3-amino-2,2-dimethylpropyl)-4-hydroxybutyric acid amide oxalate; yield 15% of theory; solvent: ethanol; m.p. 91°–93° C.

4) trans-2-amino-2-methyl-N-(2-nitroxycyclohexyl)-propionic acid amide hemifumarate from trans-2-amino-2-methyl-N-(2-hydroxycyclohexyl)-propionic acid amide oxalate; yield 20% of theory; solvent: ethanol; m.p. 159°–164° C.

5) 2-amino-N-(3-nitroxypropyl)-propionic acid amide benzoate from 2-amino-N-(3-hydroxypropyl)-propionic acid amide oxalate; yield 20% of theory; solvent: ethyl acetate; m.p. 120°–125° C.

6) trans-2-amino-2-methyl-N-(4-nitroxycyclohexyl)-propionic acid amide cyclamate from trans-2-amino-2-methyl-N-(4-hydroxycyclohexyl)-propionic acid amide oxalate; yield 75% of theory; solvent: ethanol; m.p. 188°–190° C.

7) trans-2-amino-2-methyl-N-(2-nitroxycyclohexylmethyl)-propionic acid amide fumarate from trans-2-amino-2-methyl-N-(2-hydroxycyclohexylmethyl)-propionic acid amide; yield 85% of theory; solvent: ethanol; m.p. 195°–197° C.

8) trans-2-amino-2-methyl-N-(4-nitroxymethylcyclohexyl)-propionic acid amide cyclamate from trans-2-amino-2-methyl-N-(4-hydroxymethylcyclohexyl)-propionic acid amide; yield 45% of theory; solvent: ethanol; m.p. 182°–184° C.

9) 2-dimethylamino-N-(2-methyl-2-nitroxypropyl)-acetamide fumarate from 2-dimethylamino-N-(2-methyl-2-hydroxypropyl)-acetamide; yield 54% of theory; solvent: ethanol; m.p. 102°–103° C.

10) N-(3-amino-2,2-dimethylpropyl)-2-nitroxypropionic acid amide fumarate from N-(3-amino-2,2-dimethylpropyl)-2-hydroxypropionic acid amide; yield 10% of theory; solvent: ethanol/diethyl ether; m.p. 89°–91° C.

11) trans-2-amino-N-(4-nitroxycyclohexylmethyl)-acetamide fumarate from trans-2-amino-N-(4-hydroxycyclohexylmethyl)-acetamide; yield 44% of theory; solvent: isopropanol; m.p. 132°–135° C.

12) cis-N-(2-aminoethyl)-4-nitroxycylohexanecarboxylic acid amide fumarate from cis-N-(2-aminoethyl)-4-hydroxycyclohexanecarboxylic acid amide; yield 47% of theory; solvent: ethanol; m.p. 126°–128° C.

13) trans-N-(3-aminopropyl)-4-nitroxycyclohexanecarboxylic acid amide fumarate from trans-N-(3-aminopropyl)-4-hydroxycyclohexanecarboxylic acid amide; yield 16% of theory; solvent: ethanol; m.p. 140°–142° C.

EXAMPLE 3

2-Aminocarbonylamino-2-methyl-N-(2-nitroxyethyl)-propionic acid amide 0.77 g. 2-Amino-2-methyl-N-(2-nitroxyethyl)-propionic acid amide fumarate is dissolved in 7.5 ml. methanol and 2.5 ml. water and 0.81 g. potassium cyanate added thereto. The reaction mixture is stirred for 10 minutes at ambient temperature and then 0.30 g. acetic acid added thereto. After stirring overnight, the inorganic salts are precipitated out by the addition of 25 ml. ethyl acetate and filtered off with suction. The filtrate is dried over anhydrous sodium sulphate, filtered with suction and evaporated, 0.60 g. of crude product being obtained. This is triturated with diethyl ether and filtered off with suction. There is obtained 0.40 g. of the title compound, i.e. 68% of theory; m.p. 98°–100° C.

The following compounds are obtained in an analogous manner:

1) N-aminocarbonyl-3-nitroxypropylamine from 3-nitroxypropylamine and potassium cyanate; yield 35% of theory; solvent: ethyl acetate; m.p. 77°–79° C.

2) 2,2-dimethyl-3-nitroxypropionic acid 4-aminocarbonylpiperazide from 2,2-dimethyl-3-nitroxyproprionic acid piperazide; yield 60% of theory; solvent: ethyl acetate/diethyl ether; m.p. 148°–150° C.

3) 5-nitroxyvalerianic acid 4-aminocarbonylpiperazide from 5-nitrovalerianic acid piperazide; yield 11% of theory; solvent: ethyl acetate; m.p. 106°–107° C.

4) trans-4-nitroxycyclohexanecarboxylic acid 4-aminocarbonylpiperazide from trans-4-nitroxycyclohexanecarboxylic acid piperazide; yield 20% of theory; solvent: ethanol; m.p. 180°–182° C.

5) trans-N-(2-nitroxycyclohexyl)-urea from trans-N-2-nitroxycyclohexylamine; yield 46% of theory; solvent: ethanol; m.p. 136°–139° C.

6) trans-N-(4-nitroxycyclohexyl)-urea from trans-N-4-nitroxycyclohexylamine; yield 67% of theory; solvent: isopropanol; m.p. 181°–183° C.
7) trans-N-(4-nitroxycyclohexylmethyl)-urea from trans-N-4-nitroxycyclohexylmethylamine; yield 40% of theory; solvent: ethyl acetate/diethyl ether; m.p. 82°–84° C.
8) N-aminocarbonyl-(2,2-dimethyl)-3-nitroxypropylamine from 2,2-dimethyl-3-nitroxypropylamine; yield 74% of theory; solvent: diethyl ether; m.p. 73°–75° C.

EXAMPLE 4

2-Isopropylaminocarbonylamino-2-methyl-N-(2-nitroxyethyl)-propionic acid amide 1.9 g. 2-Amino-2-methyl-N-(2-nitroxyethyl)-propionic acid amide is dissolved in 10 ml. ethyl acetate and mixed with 1.1 ml. isopropyl isocyanate while cooling with ice-water to 5° to 10° C. The reaction mixture is stirred for 2 hours at 10° C., filtered off with suction and washed with diethyl ether. There is obtained 1.4 g. of the title compound, i.e. 50% of theory; m.p. 120°–122° C.

The following compound is obtained in an analogous manner:

N-(2-isopropylaminocarbonylaminoethyl)-4-nitroxybutyric acid amide from N-(2-aminoethyl)-4-nitroxybutyric acid amide and isopropyl isocyanate; yield 50% of theory; solvent: ethyl acetate/diethyl ether; m.p. 133°–135° C.

EXAMPLE 5

The starting compounds are prepared as follows:

a) 3-Amino-N-(3-hydroxypropyl)-propionic acid amide hemioxalate 113 g. Ethyl 2-cyanoacetate are dissolved in 1 liter methylene chloride and mixed with 75.1 g. 3-amino-1-propanol. After 3 days stirring at ambient temperature, vacuum distillation is carried out. There remain 153 g. of crude 2-cyano-N-(3-hydroxypropyl)-acetamide, i.e. about 100% of theory.

61 g. of this product are dissolved in 300 ml. methanol, mixed with 300 ml. liquid ammonia and hydrogenated in the presence of 20 g. Raney nickel at 100 bar hydrogen pressure and ambient temperature. After filtering off the catalyst with suction, the solvent is distilled off in a vacuum, the residue is dissolved in 400 ml. ethanol and mixed with 19.4 g. oxalic acid in 200 ml. ethanol. After standing overnight, it is filtered off with suction. There are obtained 64.2 g. of the hemioxalate of the title compound, i.e. 78% of theory; m.p. 140°–142° C.

b) 2-Amino-2-methyl-N-(3-hydroxypropyl)-propionic acid amide 30 g. 3-Amino-1-propanol are mixed with 129 g. 2-methyl-2-nitropropionic acid methyl ester and heated in an oil bath at 120° C. for 8 hours. The excess ester is distilled off in a vacuum at 15 Torr. There remains a residue of 76 g. of crude product of 2-methyl-2-nitro-N-(3-hydroxypropyl)-propionic acid amide.

Without further purification, this is dissolved in 1 liter methanol and hydrogenated at ambient temperature and 1 bar hydrogen pressure in the presence of Raney nickel. The catalyst is filtered off with suction and the solvent is distilled off in a vacuum. There remain about 65 g. of crude base. This is dissolved in 650 ml. ethanol and mixed with 18 g. anhydrous oxalic acid. After standing overnight, the product is filtered off with suction. There are obtained 70 g. of the hemioxalate of the title compound, i.e. 85% of theory; m.p. 156°–158° C.

c) trans-2-Amino-N-(4-hydroxycyclohexyl)-acetamide 11.5 g. (0.06 mole) trans-2-chloro-N-(4-hydroxycyclohexyl)-acetamide are dissolved in 100 ml. methanol and shaken with 200 ml. liquid ammonia for 20 hours at 50° C. in an autoclave. After concentration of the solvent, suction filtration is carried out. There are obtained 9.7 g. of the title compound, i.e. 94% of theory; m.p. 110°–114° C.

The following compounds are obtained in an analogous manner:

c1) trans-3-amino-N-(4-hydroxycyclohexyl)-propionic acid amide in the form of a viscous syrup; yield 60% of theory.

c2) with dimethylamine, there is obtained trans-2-dimethylamino-D-(4-hydroxycyclohexyl)-acetamide oxalate; m.p. 148°–150° C., recrystallised from ethanol; yield 89% of theory.

d) trans-2-Chloro-N-(4-hydroxycyclohexyl)-acetamide 15.1 g. (0.1 mole) trans-4-aminocyclohexanol hydrochloride are suspended in 100 ml. water and adjusted to a pH of 12.5 by the addition of 50 ml. 2N aqueous sodium hydroxide solution. 9.5 ml. (0.12 mole) chloroacetyl chloride are then added dropwise thereto and the pH maintained at 12 to 12.5 by the simultaneous dropwise addition of 2N aqueous sodium hydroxide solution. After the end of the reaction, the reaction mixture is extracted with n-butanol and the organic phase is distilled off in a vacuum. The residue is again dissolved in ethanol, filtered, evaporated and triturated with diethyl ether. After filtering off with suction, there are obtained 12.9 g. of the title compound, i.e. 67% of theory; m.p. 149°–151° C.

d1) In an analogous manner, with the use of 3-chloropropionic acid chloride, there is obtained trans-3-chloro-N-(4-hydroxycyclohexyl)-propionic acid amide in a yield of 73% of theory; m.p. 153°–157° C., after recrystallisation from ethyl acetate.

TEST PROTOCOL

The compounds of the present invention have nitrate-like properties with a especially long duration of action and are therefore preferably useful in the treatment of anti-angina deseases, i.e. heart deseases which are characterized by pain attacks whereby the oxygen requirement of the heart has not sufficient security. Presently, there are used for the treatment of coronary heart deseases nitrate compounds, such as nitroglycerol, isosorbitdinitrate (ISDN), isosorbitmononitrate (ISMO) as well as β-blocking compounds, such as propranolol. These hitherto known compounds have however a short duration of action due to the relatively fast denitration velocity (hydrodysis of the nitrato group).

METHOD

To show denitration properties (which constitutes the working principle of all nitrates; see U. Abshagen in Handbook of Experimental Pharmacology, Vol. 76, 1985, Chapter 10.) the denitration rate was evaluated in relation to that of the known isosorbide dinitrate metabolite isosorbide-5-mononitrate ($V_{rel}$). To that end, rats were killed under narcosis and their livers reperfused 4 min with a corresponding concentrated equimolar ($5\times10^{-5}$M/l) solution of isosorbide-5-mononitrate and the substances to be tested respectively (a blood sediment solution was pumped through the liver vessels) and the freed amount in $NO_2$ determined in the perfusate (outflowing fluid). To have comparable conditions, the perfusion with isosorbide-5-mononitrate (standard substance) was administered as control at the second time as if it were an unknown substance (in this way a liver performance change under the test conditions can be recognized and accordingly allowed for).

The following table gives the results for some selected compounds:

TABLE

| compound of example | liver perfusion (relative denitration rate) $V_{rel}$ |
|---|---|
| ISMO | 0.95 |
| 1.2 | 0.54 |
| 1.14 | 0.35 |
| 1.56 | 0.55 |
| 2.6 | 0.53 |
| 3.6 | 0.32 |

The compounds according to the present invention seem to be particularly useful for the therapy because $V_{rel}$ has a sufficiently long duration of action at a comparatively low concentration (i.e. low dosage to be administered).

What is claimed is:

1. A nitroxyalkylamine compound of the formula:

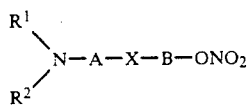

wherein $R_1$ is a straight-chained or branched, saturated or unsaturated $C_1$–$C_8$-alkyl radical, a $C_3$–$C_8$-cycloalkyl or $C_3$–$C_8$-cycloalkenyl radical, an aminocarbonyl, $C_1$–$C_6$-alkylaminocarbonyl or di-$C_1$–$C_6$-alkylaminocarbonyl radical, $R^2$ is a straight-chained or branched, saturated or unsaturated $C_1$–$C_6$-alkyl radical or a $C_3$–$C_8$-cycloalkyl or cycloalkenyl radical, A is a valency bond or a straight-chained or branched alkylene chain containing up to 8 carbon atoms, in which a —$CH_2$— group can be replaced by a cycloalkylene radical containing 3 to 7 carbon atoms, B is a straight-chained or branched alkylene chain containing 1 to 8 carbon atoms, in which a —$CH_2$— group can be replaced by a cycloalkylene group containing 3 to 7 carbon atoms and X is an —$NR^3$—CO— radical, in which $R^3$ is a hydrogen atom or a saturated or unsaturated alkyl radical containing up to 6 carbon atoms; an optically-active isomer thereof; or a pharmaceutically acceptable salt thereof.

2. A pharmaceutical composition comprising at least one nitroxyalkylamine compound of the formula:

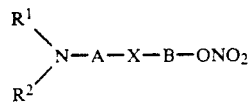

wherein $R_1$ is a hydrogen atom, a straight-chained or branched, saturated or unsaturated $C_1$–$C_8$-alkyl radical, a $C_3$–$C_8$-cycloalkyl or $C_3$–$C_8$-cycloalkenyl radical, an aminocarbonyl, $C_1$–$C_6$-alkylaminocarbonyl or di-$C_1$–$C_6$-alkylaminocarbonyl radical, $R^2$ is a hydrogen atom, a straight-chained or branched, saturated or unsaturated $C_1$–$C_6$-alkyl radical or a $C_3$–$C_8$-cycloalkyl or cycloalkenyl radical, A is a valency bond or a straight-chained or branched alkylene chain containing up to 8 carbon atoms, in which a —$CH_2$— group can be replaced by a cycloalkylene radical containing 3 to 7 carbon atoms, B is a straight-chained or branched alkylene chain containing 1 to 8 carbon atoms, in which a —$CH_2$— group can be replaced by a cycloalkylene radical containing 3 to 7 carbon atoms and X is an —$NR^3$—CO— or —CO—$NR^3$— group, in which $R^3$ is a hydrogen atom or a saturated or unsaturated alkyl radical containing up to 6 carbon atoms; an optically-active isomer thereof; or a pharmacologically acceptable salt thereof; in an amount effective to treat angina-like heart and circulatory diseases; together with a pharmaceutically acceptable carrier.

3. A pharmaceutical composition according to claim 2, wherein $R^1$ is a hydrogen atom, a straight-chained or branched $C_1$–$C_8$-alkyl radical, an aminocarbonyl or $C_1$–$C_6$-alkylaminocarbonyl radical or $R^2$ is a hydrogen atom or a straight-chained or branched $C_1$–$C_6$-alkyl radical.

4. A pharmaceutical composition according to claim 2, wherein A is a valency bond or a methylene, ethylene, trimethylene, tetraethylene, pentamethylene, hexamethylene, methylmethylene, 1-methylethylene, dimethylmethylene, 1,1-dimethylethylene, 1,1-dimethyltrimethylene, 1-methyltrimethylene, 1,1-dimethylmethylene, 1-ethylmethylene, 1,1-dimethyltetramethylene, 1,2-dimethyltrimethylene, 2,2-dimethyltrimethylene, 3,3-dimethyltrimethylene, 1,1-dimethylpentamethylene, 1,1-dimethylhexamethylene or 1-methyltetramethylene radical.

5. A pharmaceutical composition according to claim 2, wherein B is ethylene, 1-methylethylene, 2-methylethylene, trimethylene, 1-methyltrimethylene, 3-methyltrimethylene, tetramethylene, pentamethylene, 1-methyltetramethylene, 1-ethyltrimethylene, hexamethylene, 1-methylpentamethylene, 1-ethyltetramethylene, 1-n-propyltrimethylene, 1,1-dimethylethylene, dimethylmethylene, 1,1-dimethyltrimethylene, 2,2-dimethyltrimethylene, 2,2-dimethyltetramethylene or 1,1-dimethylhexamethylene, a 1,2-, 1,3- or 1,4-cyclohexylene radical, a methylene-1,2-cyclohexylene radical, a methylene-1,3-cyclohexylene radical or a methylene-1,4-cyclohexylene radical in which the configuration of the cycloalkylene radical is cis or trans.

6. A pharmaceutical composition according to claim 2, wherein $R^3$ is a hydrogen atom, a $C_1$–$C_6$-alkyl or $C_2$–$C_6$-alkenyl radical or $R^3$, together with the nitrogen atom and a carbon atom of the group A, forms a pyrrolidine or piperidine ring or $R^3$, together with $R^2$, A and the two nitrogen atoms, forms a piperazine ring.

7. A pharmaceutical composition comprising at least one nitroxyalkylamine compound as defined in claim 1 in an amount effective to treat angina-like heart and circulatory diseases, and a pharmaceutically acceptable carrier therefor.

8. A method for the prophylaxis or treatment of angina-like heart and circulatory diseases which comprises administering a composition according to claim 2 to an animal in need of such treatment.

9. A method for the prophylaxis or treatment of angina-like heart and circulatory diseases which comprises administering a therapeutically effective amount of a compound according to claim 1 to an animal in need of such treatment.

10. A compound according to claim 1, wherein A is a valency bond.

11. A pharmaceutical composition according to claim 2, wherein A is a valency bond and B is cycloalkylene.

12. A pharmaceutical composition according to claim 2, wherein the nitroxyalkylamine compound is
2-amino-N-(1-nitroxy-2-methylprop-2-yl)acetamide,
4-amino-N-(2-nitroxyethyl)-butyric acid amide,
trans-2-amino-2-methyl-N-(4-nitroxycyclohexyl)-propionic acid amide, or
trans-N-(4-nitroxycyclohexyl)-urea;
or a pharmacologically acceptable salt thereof.

13. A pharmaceutical composition comprising at least one nitroxyalkylamine compound as defined in claim 12 in an amount effective to treat angina-like heart and circulatory diseases, and a pharmaceutically acceptable carrier therefor.

* * * * *